United States Patent [19]

Mackiewicz et al.

[11] Patent Number: 5,935,569
[45] Date of Patent: Aug. 10, 1999

[54] GENETIC ANTICANCER VACCINE

[75] Inventors: Andrzej Mackiewicz, Poznań, Poland; Stefan Rose-John, Mainz, Germany

[73] Assignee: Akademia Medyczna IM. K. Marcinkowskiego, Poznan, Poland

[21] Appl. No.: 08/952,261

[22] PCT Filed: May 13, 1996

[86] PCT No.: PCT/PL96/00010

§ 371 Date: Nov. 14, 1997

§ 102(e) Date: Nov. 14, 1997

[87] PCT Pub. No.: WO96/36354

PCT Pub. Date: Nov. 21, 1996

[30] Foreign Application Priority Data

May 15, 1995 [PL] Poland .................................... 308627

[51] Int. Cl.$^6$ ............................ A01N 63/00; C12N 15/85; C12N 15/63

[52] U.S. Cl. ................... 424/93.21; 435/325; 435/320.1; 435/69.52; 424/93.3; 424/277.1; 424/85.2

[58] Field of Search .............................. 424/93.21, 277.1, 424/85.2, 93.3; 435/325, 320.1, 69.52

*Primary Examiner*—Paula K. Hutzell
*Assistant Examiner*—Geetha P. Bansal
*Attorney, Agent, or Firm*—Collard & Roe, P.C.

[57] ABSTRACT

Genetic anticancer vaccine for stimulation of patient's immune system to eradicate cancer, particularly malignant melanoma. The objective of the invention is genetic modification of allogeneic cancel cells by insertion of the two genes, one encoding human interleukin 6 and the other encoding soluble interleukin 6 receptor, which will be administered to patients.

1 Claim, No Drawings

GENETIC ANTICANCER VACCINE

The objective of the invention is genetic anticancer vaccine for gene therapy of human neoplastic diseases particularly malignant melanoma.

Concept of so called genetic cellular vaccines is based on genetic modification of autologous (patient's own) or antigenetically related (allogeneic) cancer cells in order to activate patient's imnmunologic system to eliminate cancer. Autologous (obtained from each patient to be treated) and/or allogeneic (established cancer cell lines) genetically modified cancer cells are irradiated and injected subcutaneously to the patient. Until now cancer (autologous or allogeneic) cells in order to provide costimulatory signal for patient's own immune system have been genetically modified by insertion of various genes encoding: interleukin (IL) 2 [allogeneic cells: (1)], IL-4 (2) IL-7 (3), tumor necrosis factor [TNF: (4)], interferon gamma (5) or macrophage-granulocyte colony stimulating factor [GM-CSF) (6)] (autologous cells).

1. Osanto S, Brouwenstyn N, Vaessen N, Figdor C. G, Melief C, Schrier P. I, Immunization with Interleukin-2 Transfected Melanoma Cells. A Phase I-II Study in Patients with Metastatic Melanoma. Human Gene Therapy, 4:323–330, 1993.
2. Lotze M. T, Gene Therapy of Cancer: A Pilot Study of IL-4 Gene Modified Fibroblasts Admixed with Autologous Tumor to Elicit an Immune Response. Human Gene Therapy, 5:41–56, 1994.
3. Schmidt-Wolf I, Interleukin-7 Gene Transfer in Patinets with Metastatic Colon Carcinoma, Renal Cell Carcinoma, Melanoma or Lymphoma. Human Gene Therapy 5:1161–1168, 1994.
4. Rosenberg A, Immunization of Cancer Patients Using Autologous Cancer Cells Modified by Insertion of the Gene for Tumor Necrosis Factor (TNF). Human Gene Therapy, 3:57–73, 1991.
5. Siegler H. F., A Phase I trial of Human Gamma Interferon—Transduced Autologous Tumor Cells in Patients with Disseminated Malignant Melanoma. Human Gene Therapy, 5:761–773, 1994.
6. Patent No WO 9418995 (Sep. 1, 1994): Retrovirus transduced tumor cell for producing immunomolecule—interleukin 2, interferon gamma, colony stimulating factor, adhesion molecule, tumor-associated antigen, etc., antisense RNA expression by packaging cell culture for eg tumor gene therapy.

The objective of the invention is genetic modification of human malignant melanoma cell line which is HLA-A1 and HLA-A2 positive by introduction into the cells two genes (cDNA) coding human IL-6 and soluble IL-6 receptor (sIL-6R).

SIL-6R was constructed by replacement of cytoplasmic and transmembrane domains of the membrane receptor by translational stop codon using polymerase chain reaction (PCR). Moreover, signal peptide was replaced by translational start codon ATG using PCR and introducing methionine as a first aminoacid of sIL-6R.

Another objective of the invention is a vaccine containing autologous cancer cells and genetically modified allogeneic cancer cells. Combination of autologous and allogeneic cells will increase immunogenicity and effectiveness of the vaccine. In this variant of the vaccine autologous cells do not require genetic modification. Products of introduced genes will be supplied by allogeneic cells and their biological effect will be provided by "by stander effect".

EXAMPLES OF APPLICATION OF THE INVENTION

1. From the melanoma patient (HLA-A1 and/or HLA-A2 positive) a cancer metastatic focus will be surgically excised. Obtained tissue will be minced, cells enzymatically isolated and either frozen in liquid nitrogen or cultured in vitro in typical conditions. After obtaining in culture required number of cells they will be mixed (1:1) with genetically modified allogeneic cells. If propagation of autologous cells in vitro will not be possible cells frozen in liquid nitrogen will be thawed and used. Then the mixture ($5 \times 10^7$ cells per injection) will be irradiated using a total dose of 100 Gy and subcutanousely administered to the patient. Four injections will be administered in two weeks intervals followed by three injections once a month. If necessary injections will be continued in two months intervals.

2. in some melanoma patients excision of metastases will not be possible due to the advancement of the disease or localization of lesions. In such cases allogeneic vaccine will be applied. Genetically modified cells ($5 \times 10^7$) will be irradiated and administered as described above.

What is claimed is:

1. Genetic anticancer vaccine, comprising autologous cancer cells, and genetically modified allogeneic cancer cells with two genes (cDNA), one encoding interleukin 6 (IL-6), and the other encoding interleukin 6 soluble receptor (sIL-6R), while content of allogeneic cells cannot be lower than 50% and cannot exceed 70%.

* * * * *